US006541003B1

(12) United States Patent
Smith (10) Patent No.: US 6,541,003 B1
(45) Date of Patent: Apr. 1, 2003

(54) CONDITIONALLY CONTROLLED, ATTENUATED HIV VACCINE

(75) Inventor: Stephen M. Smith, Essex Fells, NJ (US)

(73) Assignee: Infectious Diseases Foundation, Essex Fells, NJ (US)

(*) Notice: Subject to any disclaimer, the term of this patent is extended or adjusted under 35 U.S.C. 154(b) by 25 days.

(21) Appl. No.: 09/624,964

(22) Filed: Jul. 25, 2000

Related U.S. Application Data (60) Provisional application No. 60/146,085, filed on Jul. 28, 1999.

(51) Int. Cl.[7] ............................................. A61K 39/21
(52) U.S. Cl. .............................. 424/188.1; 424/208.1; 435/236
(58) Field of Search ........................... 424/188.1, 208.1; 536/23.72

(56) References Cited

PUBLICATIONS

Lee, T.–H., 1997, "Acquired immunodeficiency disease vaccines: design and development", in *AIDS: Biology, Diagnosis, Treatment, and Prevention*, fourth edition, De Vita, Jr., V.T., et al., eds., Lippincott–Raven Publishers, pp. 605–616.*
Haynes, B.F., et al., 1996, "Update on the issues of HIV vaccine development", Ann. Med. 28:39–41.*
Baba, T.W., et al., 1995, "Pathogenicity of live, attenuated SIV after mucosal infection of neonatal macaques", Science 267:1820–1825.*
Ruprecht, R., 1999, "Live attenuated AIDS viruses as vaccines: promise or peril?", Immunol. Rev. 170:135–149.*
Stahl–Hennig, C., et al., 1996, "Attenuated SIV imparts immunity to challenge with pathogenic spleen–derived SIV but cannot prevent repair of the nef deletion", Immunol. Let. 51:129–135.*
Baba, T.W., et al., 1999, "Live attenuated, multiply deleted simian immunodeficiency virus causes AIDS in infant and adult macaques", Nature Med. 5(2):194–203.*
Ertl, H.C.J. and Z.Q. Xiang, 1996, "Genetic immunization", Vir. Immunol., 9(1):1–9.*
Klinman, D.M., et al., 2000, "DNA vaccines: capacity to induce auto–immunity and tolerance", Dev. Biol., 104:45–51.*
Klinman, D.M., et al., 1997, "DNA vaccines: safety and efficacy issues", Spring. Sem. Immunopath., 19(2):245–256.*

* cited by examiner

*Primary Examiner*—Laurie Scheiner
*Assistant Examiner*—Jeffrey S. Parkin
(74) *Attorney, Agent, or Firm*—Roberts Abukhair & Mardula, LLC (57) ABSTRACT

A live attenuated human immunodeficiency virus type 1 (HIV-1) whose replication is not constitutive but is instead conditionally regulated (such that rounds of reverse transcription with accompanying potential for error are strictly limited) might yield a paradigm that minimizes evolution to virulence and facilitate vaccine development. We have broached the concept of conditional control of HIV-1 through gain-of-function. Here, we describe the design of constitutively inactive HIV-1 genomes (HIV-DoxT and HIV-DoxSp) which can be conditionally resuscitated to an active state by tetracycline or related analogues. The HIV-DoxT construct comprises an inactivating mutation engineered into TAR, thereby rendering the virus non-responsive to Tat, a 302-bp DNA fragment (TetopT) which contains the tet-operator ligated into a position upstream of the HIV TATAA box, in both the 5' and 3' LTRs, and a reverse tetracycline-controlled activator (RTTA) coding sequence in place of the nef coding region. The HIV-DoxSp construct contains three additional Sp1 sites in the TetopT promoter upstream of the TATAA box thereby generating the promoter TetopSp. Genotypically, HIVDoxT is tat(+)tar(−)nef(−)Sp1(−) and HIVDoxSp is tat(+)tar(−)nef(−)Sp1(+). Since both genomes are genetically tar(−), they would ordinarily be expected to be wholly defective in producing viral proteins and/or particles. However, following transfection into an appropriate cell target, both proviruses, in a doxycycline-dependent fashion, capably released Gag and RT from cells. In the absence of doxycycline, no replication competent virus could be recovered. These findings suggest that the heterologous RTTA+Dox mechanism substituted effectively for Tat/TAR. These constructs should prove useful in the development of HIV-specific immunological and diagnostic reagents.

6 Claims, 5 Drawing Sheets

CONDITIONALLY CONTROLLED, ATTENUATED HIV VACCINE

RELATED APPLICATION

This application claims priority of the application entitled Conditionally Controlled, Attenuated HIV-1 Vaccine Candidate, having a Ser. No. of 60/146,085 and filed on Jul. 28, 1999.

BACKGROUND OF THE INVENTION

This invention relates to the field of vaccines. More particularly, this invention is directed to a process for controlling the expression of an HIV provirus to produce a doxycycline-inducible HIV genome. The genome may be used in attenuated HIV vaccines.

Vaccination and immunization generally refer to the introduction of a non-virulent agent against which an individual's immune system can initiate an immune response which will then be available to defend against challenge by a pathogen. The immune system identifies invading "foreign" compositions and agents primarily by identifying proteins and other large molecules which are not normally present in the individual. The foreign protein represents a target against which the immune response is made.

The immune system can provides multiple means for eliminating targets that are identified as foreign. These means include humoral and cellular responses which participate in antigen recognition and elimination. Briefly, the humoral response involves B cells which produce antibodies that specifically bind to antigens. There are two arms of the cellular immune response. The first involves helper T cells which produce cytokines and elicit participation of additional immune cells in the immune response. The second involves killer T cells, also known as cytotoxic T lymphocytes (CTLs), which are cells capable of recognizing antigens and attacking the antigen including the cell or particle it is attached to.

Vaccination has been singularly responsible for conferring immune protection against several human pathogens. In the search for safe and effective vaccines for immunizing individuals against infective pathogenic agents such as viruses, bacteria, and infective eukaryotic organisms, several strategies have been employed thus far. Each strategy aims to achieve the goal of protecting the individual against pathogen infection by administering to the individual, a target protein associated with the pathogen which can elicit an immune response. Thus, when the individual is challenged by an infective pathogen, the individual's immune system can recognize the protein and mount an effective defense against infection. There are several vaccine strategies for presenting pathogen proteins which include presenting the protein as part of a non-infective or less infective agent or as a discreet protein composition.

One strategy for immunizing against infection uses killed or inactivated vaccines to present pathogen proteins to an individual's immune system. In such vaccines, the pathogen is either killed or otherwise inactivated using means such as, for example, heat or chemicals. The administration of killed or inactivated pathogen into an individual presents the pathogen to the individual's immune system in a noninfective form and the individual can thereby mount an immune response against it. Killed or inactivated pathogen vaccines provide protection by directly generating T-helper and humoral immune responses against the pathogenic immunogens. Because the pathogen is killed or otherwise inactivated, there is little threat of infection.

Another method of vaccinating against pathogens is to provide an attenuated vaccine. Attenuated vaccines are essentially live vaccines which exhibit a reduced infectivity. Attenuated vaccines are often produced by passaging several generations of the pathogen through a permissive host until the progeny agents are no longer virulent. By using an attenuated vaccine, an agent that displays limited infectivity may be employed to elicit an immune response against the pathogen. By maintaining a certain level of infectivity, the attenuated vaccine produces a low level infection and elicits a stronger immune response than killed or inactivated vaccines. For example, live attenuated vaccines, such as the poliovirus and smallpox vaccines, stimulate protective T-helper, T-cytotoxic, and humoral immunities during their nonpathogenic infection of the host.

Another means of immunizing against pathogens is provided by recombinant vaccines. There are two types of recombinant vaccines: one is a pathogen in which specific genes are deleted in order to render the resulting agent non-virulent. Essentially, this type of recombinant vaccine is attenuated by design and requires the administration of an active, non-virulent infective agent which, upon establishing itself in a host, produces or causes to be produced antigens used to elicit the immune response. The second type of recombinant vaccine employs non-virulent vectors which carry genetic material that encode target antigens. This type of recombinant vaccine similarly requires the administration of an active infective non-virulent agent which, upon establishing itself in a host, produces or causes to be produced, the antigen used to elicit the immune response. Such vaccines essentially employ non-virulent agents to present pathogen antigens that can then serve as targets for an anti-pathogen immune response. For example, the development of vaccinia as an expression system for vaccination has theoretically simplified the safety and development of infectious vaccination strategies with broader T-cell immune responses.

Another method of immunizing against infection uses subunit vaccines. Subunit vaccines generally consist of one or more isolated proteins derived from the pathogen. These proteins act as target antigens against which an immune response may be mounted by an individual. The proteins selected for subunit vaccine are displayed by the pathogen so that upon infection of an individual by the pathogen, the individuals immune system recognizes the pathogen and mounts a defense against it. Because subunit vaccines are not whole infective agents, they are incapable of becoming infective. Thus, they present no risk of undesirable virulent infectivity that is associated with other types of vaccines. It has been reported that recombinant subunit vaccines such as the hepatitis B surface antigen vaccine (HBsAg) stimulate a more specific protective T-helper and humoral immune response against a single antigen. However, the use of this technology to stimulate broad protection against diverse pathogens remains to be confirmed.

Each of these types of vaccines carry severe drawbacks which render them less than optimally desirable for immunizing individuals against a particular pathogen.

It has been observed that absent an active infection, a complete immune response is not elicited. Killed and inactivated vaccines, because they do not reproduce or otherwise undergo an infective cycle, do not elicit the CTL arm of the cellular immune response in most cases. Additionally, killed and inactivated vaccines are sometimes altered by the means used to render them inactivated. These changes can sometimes affect the immunogenicity of the antigens. Subunit vaccines, which are merely discreet components of a pathogen, do not undergo any sort of infective cycle and often do not elicit the CTL arm of the cellular immune response. Absent the CTL arm, the immune response elicited by either vaccine is often insufficient to adequately protect an individual. In addition, subunit vaccines have the additional drawback of being both expensive to produce and purify.

Attenuated vaccines, on the other hand, often make very effective vaccines because they are capable of a limited, non-virulent infection and result in immune responses involving a humoral response and both arms of the cellular immune response. However, there are several problems associated with attenuated vaccines. First, it is difficult to test attenuated vaccines to determine when they are no longer pathogenic. The risk of the vaccine being virulent is often too great to properly test for effective attenuation. For example, it is not practically possible to test an attenuated form of Human Immunodeficiency virus (HIV) to determine if it is sufficiently attenuated to be a safe vaccine. Secondly, attenuated vaccines carry the risk of reverting into a virulent form of the pathogen. There is a risk of infecting individuals with a virulent form of the pathogen when using an attenuated vaccine.

Recombinant vaccines require the introduction of an active infective agent which, in many cases, is undesirable. Furthermore, in cases where the recombinant vaccine is the result of deletion of genes essential for virulence, such genes must exist and be identified. In vaccines in which pathogen genes are inserted into non-virulent vectors, many problems exist related to the immune response elicited against the vector antigens which negatively impact the immune response elicited against the target antigen. First, the recombinant vaccine introduces a great number of vector antigens against which the immune system also responds. Secondly, the vector can be used only once per individual since, after the first exposure, the individual will develop immunity to the vector. These problems are both present, for example, in recombinant vaccines that employ vaccinia vectors such as those disclosed in U.S. Pat. No. 5,017,487 issued May 21, 1991 to Stunnenberg et al. This technology has not been universally successful against diverse pathogenic organisms and it is also complicated by the large amount of excess vaccinia antigens presented in the vaccinee. Once vaccinated with the vaccinia vector, the vaccinee cannot be effectively vaccinated again using the vaccinia vector.

Accordingly, the most effective vaccines for invoking a strong and complete immune response carry the most risk of harming the individual while the safer alternatives induce an incomplete, and are therefore, less effective immune response. Furthermore, many subunit vaccines and recombinant vaccines using non-virulent vectors to produce target proteins are most useful if a single antigenic component can be identified which is singularly protective against live challenge by a pathogen. However, both technologies require that the protective component be identified. Such identification is often both laborious and time-consuming.

A distinct advantage would exist if there were a rapid system for directly testing subunit vaccination strategies without tissue culture and in the absence of excess vector antigens. Furthermore, it would be particularly advantageous if such a system could deliver an antigen that could be presented for development of both T cell immune arms.

There is a need for a means to immunize individuals against pathogen infection which can elicit a broad, biologically active protective immune response without risk of infecting the individual. Administration of a protein or peptide does not elicit a CTL response.

HIV infection represents a great threat to the human population today. Despite the intense resources expended and efforts made to develop an effective vaccine, the problem remains intractable. No vaccine is currently available that protects an individual against HIV infection. There is a great need for a method of immunizing an individual against HIV infection. There is a great need for an effective immunotherapy method to combat the development of AIDS in HIV infected individuals.

Most of the successful viral vaccines are live, attenuated versions of the wild-type virus. These attenuated viruses replicate to a lower level than their wild-type counterparts. This low level of replication is minimally deleterious to the host, but can induce a very strong immune response.

For example, the initial polio vaccine was an inactive form of the poliovirus, which did not replicate. The immune response to this vaccine was much less than that to the later version, which was an attenuated, replicating form of poliovirus. Consequently, the live-attenuated polio viral vaccine induced protective immunity in a much higher percentage of recipients than did the inactivated polio vaccine. Other live-attenuated viral vaccines in clinical use include the measles, mumps, rubella, and chicken pox vaccines. Each of these vaccines replicates to some degree in the host. A disadvantage of live-replicating vaccines is that they can, in certain circumstances, cause diseases that the inactivated vaccines could not. In immunocompromised hosts, the live vaccines can sometimes replicate more robustly than expected and could consequently be harmful to the host.

For instance, the live-attenuated polio virus vaccine caused paralytic polio at a rate of 1 in 1 million hosts. While a sub-unit based non-replicating viral vaccine, which is incapable of infection, has been successful for hepatitis B virus (containing only the surface protein of the virus), this approach has not been successful for most viral diseases. Hence, despite the predictable but small amount of disease-inducing potential of live-attenuated vaccines, these vaccines remain the vaccines of choice.

Acquired Immune Deficiency Syndrome (AIDS) is a devastating and deadly condition that has affected millions worldwide. The condition is clinically characterized by a set of typical syndromes which manifests itself by the development of opportunistic infections such as pneumocystic caimii pneumonia, toxoplasmosis, and cytomegalovirus. Additional characteristics of the AIDS-associated syndromes are the clinical manifestation of neuropsychiatric abnormalities, AIDS encephalopathy, kidney failure of AIDS nephropathy, heart failure of AIDS cardiomyopathy and certain malignancies such as Kaposi's sarcoma or B-cell lymphoma. The etiological agent for this condition has been identified as a virus, the human immunodeficiency virus (HIV). HIV is a retrovirus, that is, it is an RNA virus that replicates by transcribing genetic information from RNA to DNA, inserting this DNA into the host genome, and ultimately forming new RNA from the pro-viral DNA template.

For HIV-1, many attempts have been made at producing a sub-unit based, particle vaccine. However, it is unclear whether this type of vaccine will generate adequate protective immunity. In the macaque model of AIDS, the sub-particle approach has consistently failed to induce protective immunity.

By contrast, in the same macaque model, the live-attenuated virus approach has worked with great efficacy. Several investigators have shown that by inoculating macaques with attenuated viruses that contain large deletions in the viral genome, the hosts developed an immune response over time and became protected from subsequent challenges with wild-type viruses.

This approach has not been extended to HIV-1 in humans for several reasons. The primary reason for this is that attenuated HIV vaccines could still replicate chronically. Chronic replication of the attenuated HIV could lead to the disease itself. Alternatively, the attenuated HIV could mutate over time and develop the ability to replicate to higher levels. The reverted vaccine could then induce disease. Finally, the reverted pathogenic vaccine could then be transmitted to other people. In short, the host would not eliminate the attenuated HIV, and, thus the potential for serious side effects is unknown.

This problem was illustrated by a series of cases in Australia wherein individuals were infected via blood products transfused from a single donor. The blood contained HIV-1 virus, which was found to have deletions in the U3 region of the LTR and in the nef-coding region. Initially, these patients, despite being infected for several years, maintained stable CD4 lymphocyte counts. Their lack of clinical progression suggested that mutations, found in this naturally defective strain of HIV-1, could be used to design an attenuated HIV-1 vaccine. However, longer follow-up of these individuals has revealed a clear decline in CD4 lymphocytes in some, accompanied by detectable viral loads. This example crystallizes the central issue confronting live-attenuated HIV-1, which is the potential of an innocuous form evolving over time into a different form that could replicate to higher levels. The evolved virus then has the potential to induce disease, which could then be transmitted to others.

PCT International Application Number PCT/US90/01515 published Oct. 4, 1990 discloses methods of immunizing an individual against pathogen infection by directly injecting polynucleotides into the individual's cells in a single step procedure. The stimulation of inoculated cells is neither disclosed nor suggested. An HIV vaccine is disclosed which consists of the introduction of polynucleotides that encode the viral protein gp120. The operability of this vaccine is not evidenced.

U.S. Pat. Nos. 5,153,202; 5,278,173 and 5,318,979 to Davis disclose the treatment of HIV with antimalarial drugs in combination with antimalarial antibiotics such as doxycycline. These combinations that include tetracycline analogs are disclosed to inhibit replication of HIV in vivo.

U.S. Pat. Nos. 5,242,820 to Lo discloses that *M. fermentans* is associated with HIV infection and is sensitive to doxycycline.

U.S. Pat. No. 5,534,413 to Lo, et al. teaches that the mycoplasma, *M. penetrans* is associated with HIV infection and is sensitive to doxycycline.

U.S. Pat. No. 5,830,876 to Weiner, et al. teaches a method for immunizing a human against HIV by administering two different DNA molecules to different cells of the human. The different DNA molecules encode different HIV structural proteins which are selected from the group consisting of gag, pol and env.

U.S. Pat. No. 5,994,108 discloses the utilization of trans-dominant HIV tat substitution and truncated gene mutants of amino acid residues as pharmaceutical agents. The disclosure teaches the removal of at least 72 amino acids from the HIV virus in order to utilize the mutant virus as a possible vaccine.

U.S. Pat. No. 6,015,661 is directed toward immunologic and nucleic acid based methodologies for the detection of non-pathogenic human immunodeficiency virus type 1 (HIV-1) strains in the body fluids of HIV-infected individuals.

SUMMARY OF THE INVENTION

An object of the invention is to provide an attenuated HIV vaccine with minimal risk of uncontrolled replication. Another object of the invention is to engineer an HIV proviral plasmid cloned to allow the production of the controlled virus in the presence of a tetracycline analogue such as doxycycline. The vaccination process comprises the co-administration of an attenuated provirus and a tetracycline analogue, particularly doxycycline, to form a controlled attenuated virus in the body. The attenuated virus of the present invention is removed from the body after stopping the availability of the tetracycline analogue.

Another object of the invention is to administer doxycycline with an attenuated provirus for a limited period of time sufficient to induce an immune response. The attenuated provirus is capable of forming the virus, and thus eliciting an immune response against infection by HIV, only when administered with tetracycline analogs such as doxycycline.

There exists a serious need for an attenuate HIV vaccine that would provide induced protective immunity against human immunodeficiency virus while reducing and/or eliminating the risks of long term side effects and transmittal.

One embodiment of the present invention provides an attenuated HIV vaccine comprising an HIV provirus modified to produce the corresponding virus only in the presence of at least one tetracycline analogue. In another embodiment, the present invention provides a method for immunization of humans against HIV which comprises administering to a human a vaccine including an HIV proviral plasmid modified to produce the HIV virus only in the presence of at least one tetracycline analogue. Simultaneously, at least one tetracycline analogue is administered for a period of time to allow production of the modified HIV virus in vivo sufficient to produce immunity. Preferably, the tetracycline analogue is doxycycline.

Amongst the structural and regulatory proteins encoded by HIV is a transacting polypeptide termed the Trans-Activator of Transcription or TAT, which acts by binding to a specific region of the genomic RNA near to the long terminal repeat (LTR) termed the TAR (trans-activation response region). The action of TAT, a polypeptide of some 86–101 amino acid residues, promotes viral RNA synthesis, so that blocking of its action presents a potential therapeutic target. We and others have previously introduced the concept of controlling simian immunodeficiency virus (SIV) and HIV-1 replication through a gain-of-function approach. Through the addition to the proviral genome of the herpes simplex virus type 1 enzyme, thymidine kinase, HIV-1 and SIV can be made sensitive to the drug, ganciclovir. In vitro infection with HIV-1-TK and SIV-TK can be eliminated by ganciclovir. However, the gene for thymidine kinase was quickly deleted during reverse transcription.

HIV-Dox will produce virus in the presence of doxycycline. When doxycycline is removed, the HIV-Dox stops producing virus.

The present invention is designed to provide an HIV vaccine. This is achieved by providing a means for the control of the expression of an HIV provirus in producing a doxycycline-inducible HIV-1 genome. Using the present invention, a vaccine is provided which contains an attenuated HIV-1 provirus wherein the production of the virus in the host is under the control of another drug, namely tetracycline analogues such as doxycycline. Specifically, the virus is produced only in the presence of the drug. When the drug is no longer administered, the virus in no longer produced. Further, the produced virus does not uncontrollably replicate in the body. Replication is inhibited in the absence of the tetracycline analogue.

In the wild-type HIV, the replication process is dependent on the interaction of the protein, TAT, and on the TAR RNA region. In the HIV used in the present invention, the Tar region has been mutated such that TAR no longer interacts with TAT. This mutation essentially kills the HIV.

In accordance with one embodiment of the present invention, the first portion (U3 region) of the HIV is modified to contain a sequence that allows binding of reverse tetracycline transactivator (RTTA). This protein will bind to the specific DNA sequence only in the presence of doxycycline. When the RTTA is bound to the DNA sequence, it promotes transcription of production of the HIV RNA, which gives rise to all the HIV proteins and genome. The gene of the RTTA is placed within the HIV genome forming HIV-Dox. HIV-Dox will produce virus in the presence of doxycycline. When doxycycline is removed, the HIV-Dox stops producing virus.

In accordance with one embodiment, the HIV-Dox and the drug, doxycycline, are given simultaneously to the host. The administration of doxycycline is for the period of time needed to induce an immune response and is then discontinued. After the discontinuation of the drug, the HIV-Dox stops replicating and the HIV-Dox is then eliminated from the host, drastically reducing the possibility of long-term effects.

In accordance with another embodiment of the present invention, cells are removed from the host body and transfected with the provirus to produce the controlled virus. The transfected cells are reintroduced to the body inducing an immune response to the viral disease.

DESCRIPTION OF THE PREFERRED EMBODIMENTS

For the purposes of this application, a "tetracycline analogue" is any one of a number of compounds that are closely related to tetracycline (Tc) and which bind to the tet repressor with a Ka of at least about $10^6$ M$^{-1}$. Preferably, the tetracycline analogue binds with an affinity of about $10^9$ M$^{-1}$ or greater. Examples of such tetracycline analogues include, but are not limited to those disclosed by Hlavka and Boothe, "The Tetracyclines," in Handbook of Experimental Pharmacology 78, R. K. Blackwood et al. (eds.), Springer Verlag, Berlin-N.Y., 1985; L. A. Mitscher "The Chemistry of the Tetracycline Antibiotics, Medicinal Research 9, Dekker, N.Y., 1978; Noyee Development Corporation, "Tetracycline Manufacturing Processes," Chemical Process Reviews, Park Ridge, N.J., 2 volumes, 1969; R. C. Evans, "The Technology of the Tetracyclines," Biochemical Reference Series 1, Quadrangle Press, New York, 1968; and H. F. Dowling, "Tetracycline," Antibiotics Monographs, no. 3, Medical Encyclopedia, New York, 1955; the contents of each of which are fully incorporated by reference herein. Examples of tetracycline analogues include anhydrotetracycline, doxycycline, chlorotetracycline, epioxytetracycline, and the like. Certain tetracycline analogues, such as anhydrotetracycline and epioxytetracycline, have reduced antibiotic activity compared to tetracycline.

One embodiment of the present invention provides an attenuated HIV vaccine comprising an HIV plasmid modified to produce a controlled virus only in the presence of at least one tetracycline analogue. In another embodiment, the present invention provides a method for immunization of humans against HIV which comprises administering to a human a vaccine including an HIV plasmid modified to produce the virus only in the presence of at least one tetracycline analogue. Simultaneously, at least one tetracycline analogue is administered for a period of time to allow the production of the modified HIV virus in vivo sufficient to produce immunity. Preferably, the tetracycline analogue is doxycycline.

The introduction of the provirus of the present invention into body cells with the tetracycline analogue leads to the controlled production of the corresponding virus. Production of the virus is stopped in the absence of the tetracycline analogue. Replication of the virus, and the associated risks are inhibited in the absence of the tetracycline analogue. The replication is either completely eliminated or limited to degrees below the levels of generating a risk of infection.

Additionally, the present invention provides a process for the production of the promoter, TetopTCAT, which comprises providing a HIV-1 LTR Cat construct containing a Tar sequence, tetO sequences, and having only the HIV-1 TATAA box of the U3 region. The Tar sequence is mutated to change nucleotides +24 to +32 from TGAGCCTGG to CCTCGGACC. The tetO sequences are positioned upstream of the TATAA box to produce TetopTCAT. The production of the promoter, TetopSpCAT comprises adding three Sp1-cognate motifs between the tetO sequences and the TATAA box in the TetopTCAT. The preparation of a doxycycline-regulated HIV-1 provirus, pHIV-DoxT, comprises cloning the TetopTCAT promoter prepared above in the 3'LTR of pNL4-3 to substitute the TetopTCAT promoter for the wild-type LTRs from U3 through R. The coding sequence for RTTA was introduced into the nef reading frame to produce pHIV-DoxT.

The preparation of a doxycycline-regulated HIV-1 provirus, pHIV-DoxSp, comprises cloning the TetopSpCAT promoter prepared above in the 5'LTR or the 3'LTR of pNL4-3 to substitute the TetopSpCAT promoter for the wild-type LTRs from U3 through R. The coding sequence for RTTA was introduced into the nef reading frame to produce pHIV-DoxSp.

The process for the production of doxycycline-inducible HIV-1 genome comprises transfecting the doxycycline-regulated proviruses pHIV-DoxT in cells which support the production of the controlled virus of these proviruses in the presence of doxycycline to produce HIV-DoxT. The cells are 293-T or HeLa cells.

The process for the production of a doxycycline-inducible HIV-1 genome comprises transfecting the doxycycline-regulated proviruses pHIV-DoxSp in cells which support the production of the controlled virus of these proviruses in the presence of doxycycline to produce HIV-DoxSp. The cells are again the 293-T or HeLa cells. An injectable pharmaceutical carrier is utilized to administer an immunizing effective amount of the virus.

The method of preventing HIV-1 infection comprises administering a combination of an immunizing effective amount of the vaccine in combination with an amount of doxycycline (a tetracycline analogue) to cause the replication of the virus genome present in the vaccine. The introduction of doxycycline is continued for a time sufficient to produce immunity in the host. Subsequently, the administration of doxycycline is discontinued. It is expected that standard dosages of the tetracycline analogues is applicable in the present invention. For example, the normal dose for doxycycline of 100 mg by mouth twice per day for a period of approximately 3–6 months is applicable.

The proviral plasmids, pHIVDoxT and pHIVDoxSp, were constructed using cloning techniques similar to those described in Huang et al. Huang, L. M., A. Joshi, R. Willey, J. Orenstein, and K. T. Jeang. 1994. Human immunodeficiency viruses regulated by alternative trans-activators: genetic evidence for a novel non-transcriptional function of Tat in virion infectivity. Embo J. 13:2886–96.

Preparation of doxycycline-regulated HIV-1 promoters.

In the wild-type HIV operon, the tetracycline repressor (tetR) binds to the tetracycline operator (tetO) sequences in the absence of tetracycline and blocks transcription from the tetracycline promoter. In the presence of tetracycline, the tetR does not bind to the tetO sequences and transcription from the tet operon promoter can occur. In the past, tetR has been used with a trans-activating protein from herpes simplex virus (VP-16). This fusion protein, called tetracycline-controlled transactivator (TTA), binds specifically and conditionally to the tetO sequences. When bound to the operator DNA, TTA activates the adjacent promoters. This system permits the conditional expression of proteins, based on the presence or absence of tetracycline. A mutated version of the TTA has been created which has an opposite phenotype with respect to tetracycline-induced tetO binding. This modified transactivator is called RTTA for reverse tetracycline-controlled transactivator. RTTA binds to the tetO sequences only in the presence of tetracycline. In the absence of tetracycline, RTTA does not bind to tetO sequences and the adjacent promoter is not activated.

The RTTA system can also be used to tightly and to conditionally regulate protein expression based on the presence or absence of tetracycline or doxycycline, a tetracycline derivative.

Two versions of doxycycline-regulated HIV-1 proviruses (HIV-Dox) were prepared. As shown below, and as seen from FIGS. 2 and 3, it has been unexpectedly found that RTTA can slightly activate tetO-containing promoters even in the absence of doxycycline. Furthermore, because most promoters are less activatable after integration into cellular chromosomes, two promoter formats were tested.

The first format, tetopT, was designed to be a less potent promoter which might be activated to a lower extent, but would theoretically be more tightly regulated by doxycycline.

The second, tetopSp, would have higher promoter activity that TetopT, but would be less tightly regulated by doxycycline. Both were prepared in order to empirically assess which of the two alternatives might be best for an HIV-provirus.

The first hybrid promoter was developed from the HIV-1 long terminal repeat (LTR) and the tetO sequences. Starting with an HIV-1 LTR Cat construct, which contained only the HIV-1 TATAA box of the U3 region, the Tar sequence was mutated in a manner previously shown to abrogate Tat-responsiveness, i.e., nucleotides +24 to +32 were changed from TGAGCCTGG to CCTCGGACC. The tetO sequences were then positioned upstream of the TATAA box. This construct is called TetopCAT, and can be seen pictorially in FIG. 1.

The second hybrid promoter was formed by adding three Sp1-cognate motifs between the tetO sequences and the HIP-1 TATAA box. This construct is called TetopSpCAT, and can be seen pictorially in FIG. 2.

EXAMPLE I

Transactivation of TetopT with RTTA

With reference to FIG. 3, TetopTCAT was co-transfected into HeLa cells with either pUC (lanes 1 and 4), a Tat-expression vector (lanes 2 and 5), or an RTTA-expression vector (lanes 3 and 6) in duplicate wells. Doxycycline was added to one well (lanes 4, 5 and 6) of each co-transfection at 24 hours. At 48 hours, a CAT assay on protein extracts from each transfection was performed. Tat had no effect on CAT production. RTTA co-transfection resulted in acetylation of 6% of the chloramphenicol in the absence of doxycycline. This level of activation increased to 38% (7.7 fold) with doxycycline induction. TetopT had very low basal activity.

EXAMPLE II

Transactivation of TetopSp with RTTA

With reference to FIG. 4, TetopSpCAT was co-transfected with pUC (lanes 1 and 4), an RTTA-expression vector (lanes 2 and 5) and a Tat-expression vector (lanes 3 and 6). Half of the wells were treated with doxycycline (lanes 4, 5 and 6). Tat and the pUC control had no effect on CAT acetylation. RTTA in co-transfection resulted in nearly 100% acetylation, regardless of doxycycline induction. TetopSp had very low basal activity.

Construction of doxycycline-regulated HIV-1 proviruses.

With reference to FIG. 5, full-length HIV-1 genomes containing the tetopT and tetopSp promoters were created. The tetopT on the tetopSp were placed in the 3'LTR. The tetopSp promoter was cloned in the 5'LTR of pNL4-3. In both cloning formats, the wild-type LTRs from U3 through R were substituted with the novel promoters. Additionally, the coding sequence for RTTA was placed into the nef reading frame. The resulting proviruses were called pHIV-DoxT and pHIV-DoxSp. FIG. 5 shows a schematic illustration of these constructs, which differ only in their 3'LTRs. Since the 5'U3 region is not maintained after reverse transcription, HIV-DoxT would, after the first round of reverse transcription, have no Sp1 boxes in either LTR. The LTRs have been altered and TAR has been mutated. The gene for RTTA is inserted into the nef reading frame. The other viral reading frames remain unchanged. pHIV-DoxT and pHIV-DoxSp differ only in the 3'LTR where pHIV-DoxSp has 3 Sp1 boxes.

Each of the proviruses produced as above were transfected into 293-T and HeLa cells by known methods. Following transfection into 293-T or HeLa cells, both proviruses released gag (as measured by a CA-p24 ELISA) and reverse transcriptase (as measured by an enzymatic RT assay) into the supernatant. Gag and RT production were dependent upon the presence of doxycycline.

EXAMPLE III pHIV-DoxT was transfected into 293-T cells in duplicate plates on Day0. Doxycycline (final concentration 1 meg/ml) was added to one half of the plates on Day 1. On Day 2, p24 levels in each supernatant were determined. The supernatant from the doxycycline-treated cells had 50 ng/ml of p24. Supernatant from the untreated cells contained 500 pg/ml of p24.

Figure 1:
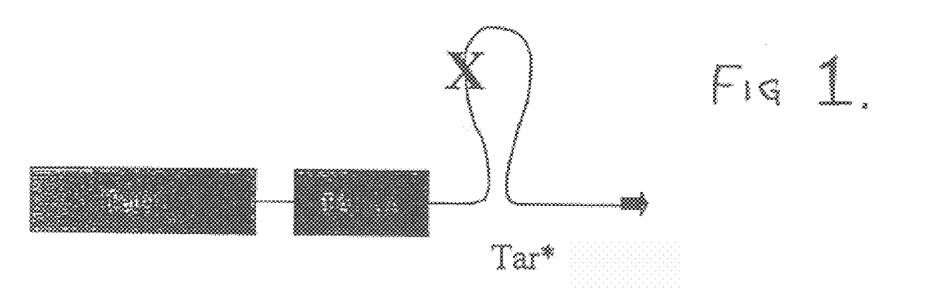
FIG. 1 is a schematic illustration of TetopT promoter with mutation in Tar in accordance with one embodiment of the present invention.
Figure 2:
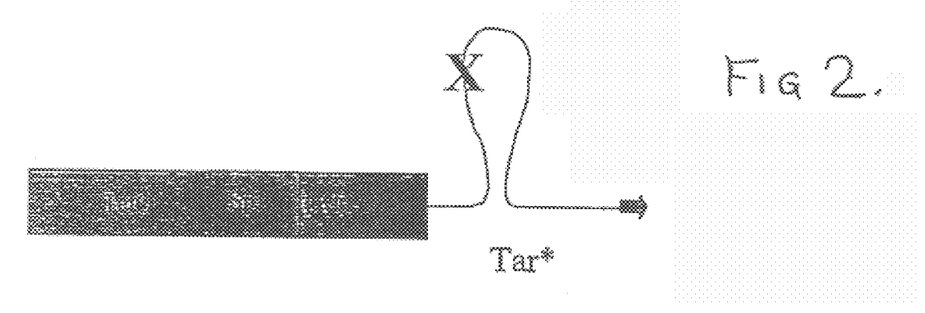
FIG. 2 is a schematic illustration of TetopSp promoter with mutation in Tar in accordance with one embodiment of the present invention.
Figure 3:
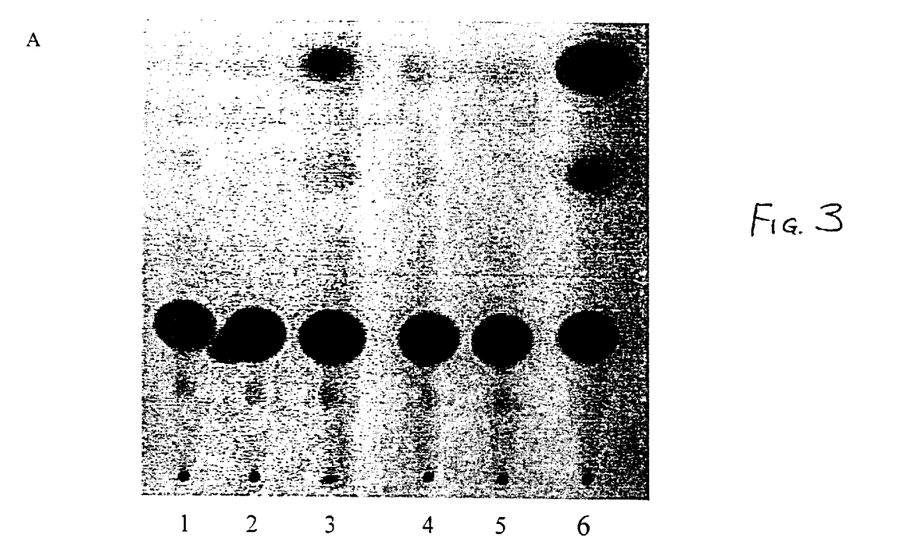
FIG. 3 is photograph showing CAT production from TetopT caused by a plasmid expressing RTTA in the absence and presence of doxycycline in accordance with one embodiment of the present invention.
Figure 4:
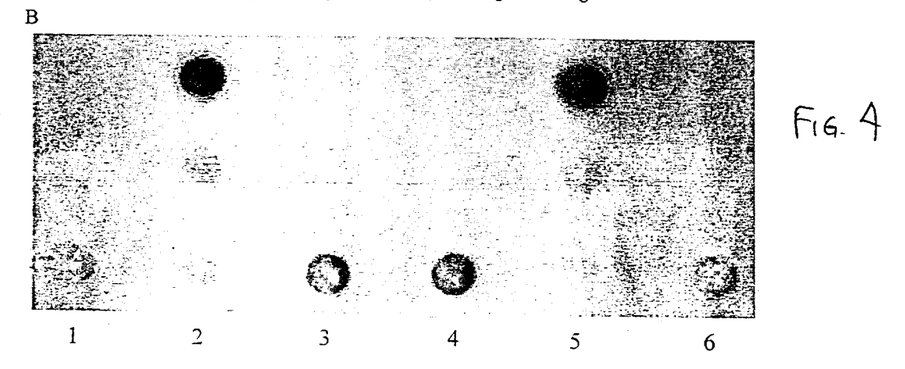
FIG. 4 is a photograph showing CAT production from TetopSp caused by a plasmid expressing RTTA in the absence and presence of doxycycline in accordance with one embodiment of the present invention.
Figure 5:
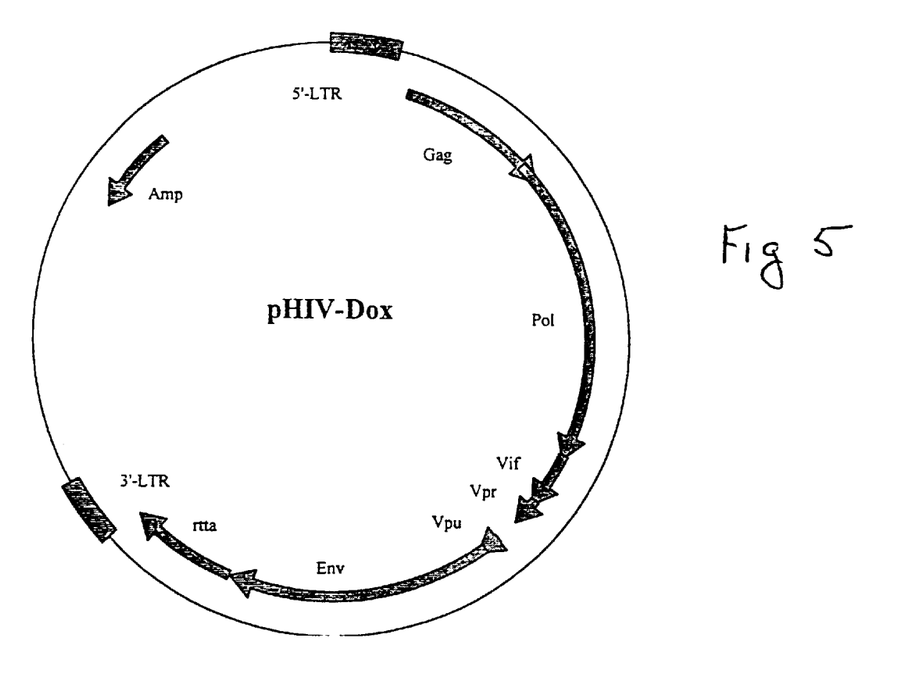
FIG. 5 is a map of pHIV-Dox in accordance with one embodiment of the present invention.
Figure 6:
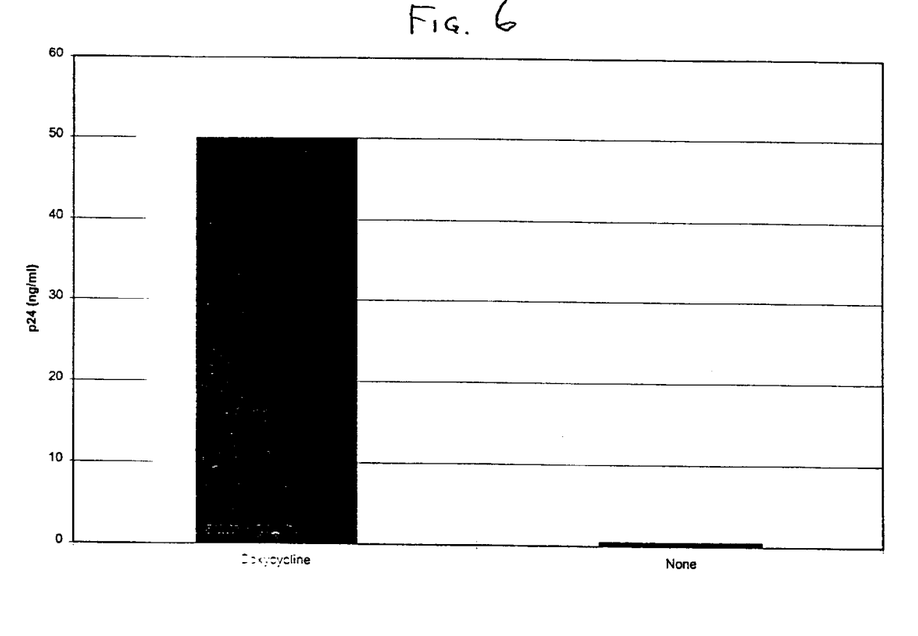
FIG. 6 is a chart showing the effect of doxycycline on the expression of HIV-Dox by HIV-DoxT in accordance with one embodiment of the present invention.

As shown in FIG. 6, the level of HIV-Dox produced by doxycycline induction after transient transfection was exceeded 100-fold. However, preliminary results indicate that neither HIV-DoxT nor HIV-DoxSp replicated efficiently in CD4+T cell lines (either in the presence or absence of doxycycline). Currently, a spreading virus infection could not be reliably measured by p24 or RT assays.

Vaccines containing HIV-Dox are prepared in accordance with the above. SIV-Dox from the corresponding simian immunodeficiency virus (SIV) can also be prepared in a like manner. An immunizing amount of the HIV-Dox (or SIV-Dox) is added to a pharmaceutically injectable carrier and administered to a host. The HIV-Dox vaccine and the drug, doxycycline, are given simultaneously. The doxycycline is given for a period necessary to induce immunity. After this time, the doxycycline is discontinued. After the doxycycline is discontinued, the HIV-Dox stops replicating. The HIV-Dox is then eliminated from the host, reducing the possibility of long term effects.

Figure 7:
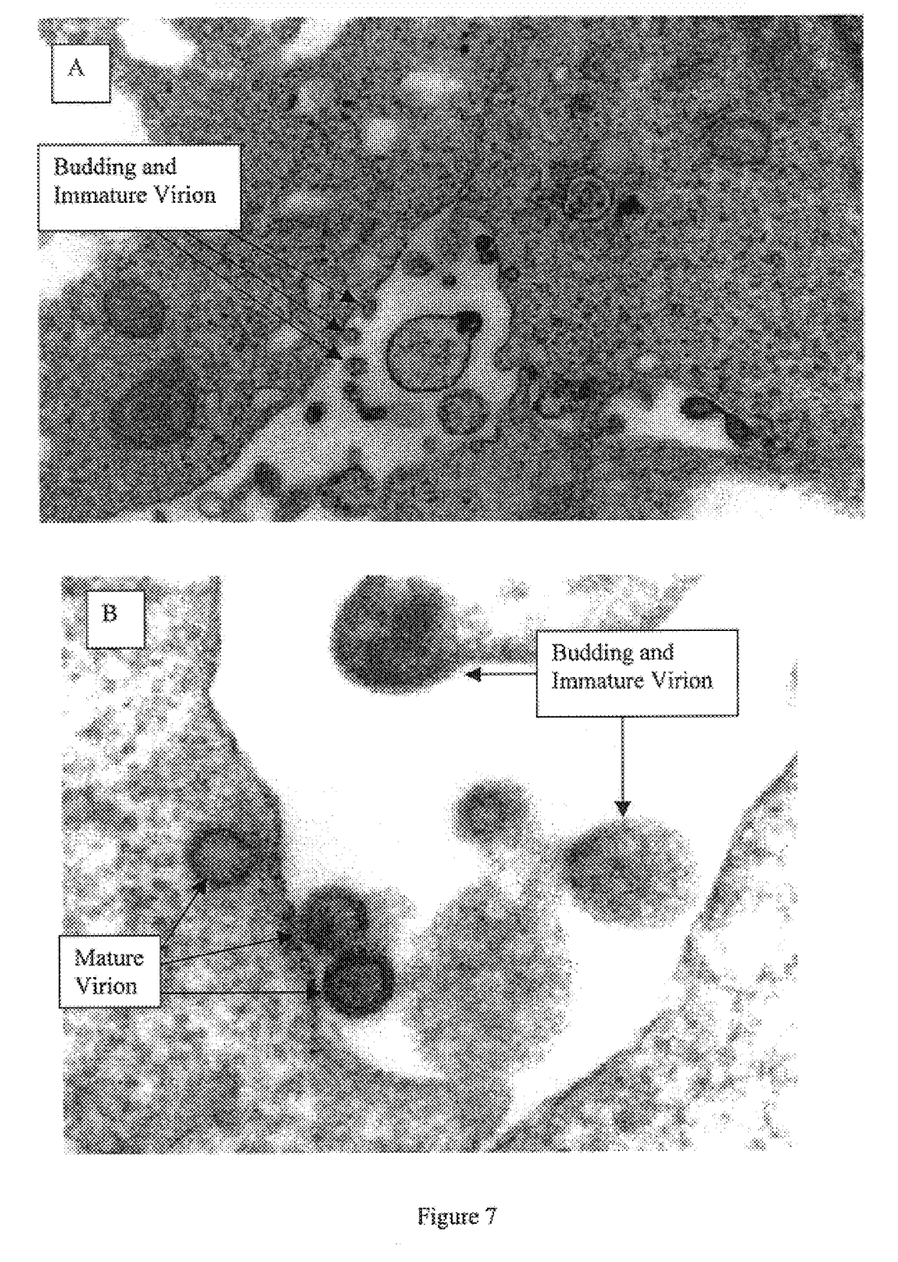
FIG. 7 shows the electron microscope images of an HIV virus produced in accordance with one embodiment of the present invention.

To assess release and maturation of viral particles, we used electron microscopy (EM). 293T cells were transfected with pNL4-3 (positive control), pHIV-DoxT, and pHIV-DoxSp. Following transfection, the HIV-Dox transfected cells were exposed to doxycycline (2 μg/ml). All transfected wells produced Gag as confirmed by p24 Elisa on the culture supernatant. The cells were fixed with glutaraldehyde and EM was performed and interpreted. As shown in FIG. 7, HIV-Dox proviruses produced mature virus particles with a normal release pattern. pHIV-DoxT produced similar mature and immature virus particles.

FIG. 7 shows that HIV-Dox produces normal viral particles. On Day 2 after transfection the cells were fixed with glutaraldehyde. Electron microscopy was performed. Panel A shows budding and immature virion. Panel B shows mature and immature virion.

The data confirm that normal, mature virus particles are produced by pHIVDox and pHIVDoxT. In other words, these data prove that virus particles, not only viral proteins, are produced by pHIVDoxT and pHIVDoxSp and that this production is conditionally regulated by doxycycline. This observation is important in vaccine development. HIV vaccines may need to produce many or all of the viral proteins in a natural form in order to elicit protective immunity, as is achieved with pHIVDoxT and pHIVDoxSp.

In accordance with another embodiment of the present invention, the HIV virus replication in the host is controlled in the presence of the tetracycline analogue.

Although the invention has been described and illustrated in detail, it is to be clearly understood that the same is by way of illustration and example, and is not to be taken by way of limitation. The spirit and scope of the present invention are to be limited only by the terms of the appended claims. For example, various proviruses may be introduced into the host body to produce the different corresponding viruses. This expands the generated immune response. Additionally, cells are optionally removed from the host body. The removed cells are transfected with the process of the present invention. The transfected cells are reintroduced into the host to induce the immune response. The removed cells are optionally transfected with more than one provirus thus inducing an immune response to more than one virus. Production of the virus and any associated replication potential are inhibited in the absence of the tetracycline analogues.

I claim:

1. An immunizing composition comprising a plasmid encoding an attenuated, doxycycline-inducible proviral molecular clone of the human immunodeficiency virus type 1 (HIV-1) and a pharmaceutical carrier, wherein said HIV-1 provirus has the following structural features: (i) a TetopSp promoter which comprises a modified HIV-1 Tar sequence, which is no longer Tat-responsive, wherein nucleotides +24 to +32 have been mutated from TGAGCCTGG to CCTCGGACC, tetO sequences, SP1-cognate binding motifs, and the HIV-1 TATAA box, the SP1-cognate binding motifs are placed between the tetO and TATAA box, and said promoter is inserted into the 5' and 3' long terminal repeats (LTRs); (ii) a reverse tetracycline transactivator (RTTA) coding region inserted into the nef coding region.

2. The composition of claim 1 wherein the plasmid is pHIV-DoxSp.

3. An immunizing composition comprising a plasmid encoding an attenuated, doxycycline-inducible proviral molecular clone of the human immunodeficiency virus type 1 (HIV-1) and a pharmaceutical carrier, wherein said HIV-1 provirus has the following structural features: (i) a TetopT promoter which comprises a modified HIV-1 Tar sequence, which is no longer Tat-responsive, wherein nucleotides +24 to +32 have been mutated from TGAGCCTGG to CCTCGGACC, tetO sequences and the HIV-1 TATAA box, wherein the tetO sequences are positioned upstream of the TATAA box, and the TetopT promoter is inserted into the 5' and 3' long terminal repeats (LTRs); (ii) a reverse tetracycline transactivator (RTTA) coding region inserted into the nef coding region.

4. The composition of claim 3 wherein the plasmid is pHIVDoxT.

5. A method for inducing an immune response to HIV-1 in a non-human host comprising:

administering the immunizing composition of claim 1 or 3 in combination with doxycycline to induce viral expression from the modified proviral construct;

continuing doxycycline administration for a period of time sufficient to induce an HIV-1-specific immune response; and discontinuing doxycycline administration after generation of the immune response;

wherein said method results in a measureable and detectable HIV-1-spcific immune response.

6. A method for inducing the expression of an attenuated human immunodeficiency virus type 1 (HIV-1) in a non-human host comprising:

administering the composition of claim 1 or 3 in combination with doxycycline to induce viral expression from the modified proviral construct; and continuing doxycycline administration for a period of time sufficient to induce stable expression of the attenuated HIV-1;

wherein said method results in the production of measurable quantities of the attenuated HIV-1.

* * * * *

UNITED STATES PATENT AND TRADEMARK OFFICE
CERTIFICATE OF CORRECTION

PATENT NO. : 6,541,003 B1
DATED : April 1, 2003
INVENTOR(S) : Stephen M. Smith

It is certified that error appears in the above-identified patent and that said Letters Patent is hereby corrected as shown below:

<u>Title page, Item [54] and Column 1, lines 1 and 2,</u>
Title, "CONDITIONALLY CONTROLLED, ATTENUATED HIV VACCINE" should read -- ATTENUATED, DOXYCYCLINE-INDUCIBLE HUMAN IMMUNODEFICIENCY VIRUS PROVIRAL MOLECULAR CLONES --
Item [74], *Attorney, Agent or Firm*, "Roberts Abukhair & Mardula, LLC" should read -- Roberts Abokhair & Mardula, LLC --

Signed and Sealed this

Twenty-ninth Day of July, 2003

JAMES E. ROGAN
*Director of the United States Patent and Trademark Office*